United States Patent
Engel et al.

(10) Patent No.: US 8,921,318 B2
(45) Date of Patent: Dec. 30, 2014

(54) APPLICATION OF INITIAL DOSES OF LHRH ANALOGUES AND MAINTENANCE DOSES OF LHRH ANTAGONISTS FOR THE TREATMENT OF HORMONE-DEPENDENT CANCERS AND CORRESPONDING PHARMACEUTICAL KITS

(75) Inventors: Jürgen Engel, Alzenau (DE); Oliver Bauer, Frankfurt (DE)

(73) Assignee: Aeterna Zentaris GmbH, Frankfurt (DE)

( * ) Notice: Subject to any disclaimer, the term of this patent is extended or adjusted under 35 U.S.C. 154(b) by 785 days.

(21) Appl. No.: 11/834,707

(22) Filed: Aug. 7, 2007

(65) Prior Publication Data

US 2008/0032935 A1    Feb. 7, 2008

Related U.S. Application Data

(60) Provisional application No. 60/909,730, filed on Apr. 3, 2007, provisional application No. 60/835,910, filed on Aug. 7, 2006.

(51) Int. Cl.
| | |
|---|---|
| *A61K 38/09* | (2006.01) |
| *A61P 5/04* | (2006.01) |
| *A61K 38/24* | (2006.01) |
| *C07K 7/23* | (2006.01) |

(52) U.S. Cl.
CPC .. *A61K 38/09* (2013.01); *C07K 7/23* (2013.01)
USPC ......... 514/10.3; 514/10.4; 514/10.6; 530/313

(58) Field of Classification Search
CPC ........ Y10S 514/80; A61K 38/09; C07K 7/23; C12Y 304/21077; G01N 33/57434
See application file for complete search history.

(56) References Cited

U.S. PATENT DOCUMENTS

| | | | |
|---|---|---|---|
| 5,663,145 A * | 9/1997 | Engel et al. | ...................... 514/15 |
| 6,455,499 B1 | 9/2002 | Roeske | |
| 2005/0159361 A1 | 7/2005 | Hara et al. | |
| 2006/0281685 A1 * | 12/2006 | Bernd et al. | ................... 514/15 |

OTHER PUBLICATIONS

Msaouel et al. (Expert Opinion Emerging Drugs, May 2007 12:258-299).*
Emmons et al. (Endocrine Related Cancers 2003 10:291-299).*
Aeterna Zentaris, Inc (www.zentaris.com, Ozarelix 2004).*
Montironi et al. (Virchows Arch. 2000 436:297-304).*
American Heritage Dictionary of the English Language, Fourth Ed 2000, prophylaxis).*
Byers, T. (CA Journal, vol. 49, No. 6, Nov./Dec. 1999).*
Cotterchio et al, 2000, Chronic Diseases in Canada, (Electronic Version downloaded from www.phac-aspc.gc.ca/publicat/cdic-mcc/21-2/f_e.html).*
Martin et al (Journal of the National Cancer Institute, 92:1126-1135).*
Hudson et al. (The J. of Urology 1989: 142: 1011-1017).*
Cohen (Int J Radiat Oncol Biol Phys, 1987, 13:251-8).*
U.S. Appl. No. 12/394,374, filed Feb. 27, 2009, Engel.
Hermann M. Behre, et al., "High Loading and Low Maintenance Doses of a Gonadotropin-Releasing Hormone Antagonist Effectively Suppress Serum Luteinizing Hormone, Follicle-Stimulating Hormone, and Testosterone in Normal Men", Journal of Clinical Endocrinology and Metabolism, vol. 82, No. 5 (1997), pp. 1403-1408.
Taiwanese Search Report dated Dec. 22, 2010, for Taiwan Invention Patent Application No. 09612903.
International Search Report dated Mar. 19, 2008, for PCT/EP2007/058156.

* cited by examiner

*Primary Examiner* — Peter J Reddig
(74) *Attorney, Agent, or Firm* — K&L Gates LLP; Louis C. Cullman; Hal Gibson

(57) ABSTRACT

LHRH analogs and LHRH antagonists for use in the treatment or prophylaxis of hormone-dependent cancers, in particular prostate cancer, prostate carcinoma and/or advanced prostate carcinoma, by administering an initial dose of an LHRH analog over a first period sufficient to effect hormonal castration, then administering a maintenance dose of an LHRH antagonist over a second period, the dose being insufficient to achieve and/or maintain hormonal castration.

12 Claims, No Drawings

APPLICATION OF INITIAL DOSES OF LHRH ANALOGUES AND MAINTENANCE DOSES OF LHRH ANTAGONISTS FOR THE TREATMENT OF HORMONE-DEPENDENT CANCERS AND CORRESPONDING PHARMACEUTICAL KITS

REFERENCE TO PRIOR APPLICATIONS

This application claims priority to U.S. provisional application 60/835,910 filed Aug. 7, 2006, and 60/909,730 filed Apr. 3, 2007, and to EP patent application 06016481.1 filed Aug. 8, 2006, all incorporated herein by reference.

FIELD OF THE INVENTION

The invention relates to compositions and methods for the treatment or prophylaxis of hormone-dependent cancers, including the application of initial doses of LHRH analogues and maintenance doses of LHRH antagonists, and corresponding pharmaceutical kits. These compositions, methods, doses and kits are useful in the treatment or prophylaxis of hormone-dependent cancers such as prostate cancer, prostate carcinoma and advanced prostate carcinoma.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

At present, the substances Zoladex® (INN: goserelin), Decapeptyl® (INN: triptorelin) and Lupron® (INN: leuprolide) are available for the therapy of hormone-dependent malignant diseases.

Zoladex® is injected under the skin in the form of an elongate cylinder 1 cm in length and 1 mm in diameter using a special applicator. Decapeptyl® is available in the form of a microcapsule emulsion which is likewise given subcutaneously. Lupron® is injected once every 4-month as a depot formulation. All forms ensure a continuous release of active compound to the surrounding tissue. The mechanism of action of all three substances is that of a superagonist.

The substance cetrorelix (INN) is an antagonist of LHRH. The mechanism of action differs completely from the known superagonists. Synthesis and some important pharmacological actions are described in U.S. Pat. No. 4,800,191 and U.S. Pat. No. 5,198,533. Other doses are therefore needed for therapy with cetrorelix.

For the complete suppression of the hormone concentration to castration level, a dose of 10 mg daily is necessary in volunteer tests amounting to at least 300 mg per month. This high daily dose cannot be accepted in sustained-release forms which are intended to act for a relatively long period of time, for example several months. The depot to be injected below the skin would be too voluminous and would no longer be tolerable.

U.S. Pat. No. 5,663,145 describes the use of initial high doses and maintenance doses of both LHRH antagonists in an animal study and volunteer trial. There, it is claimed that in DMBA-induced mamma-carcinoma in the rat with an initial high dose and a further dose which given by itself is not active, a therapeutic result could be achieved.

Further, in a volunteer trial over a period of three weeks, it was found that after the injection of an initial dose of 10 mg LHRH antagonist, which led to a complete suppression of LH, FSH and testosterone, a complete suppression of LH, FSH and testosterone could likewise be observed with maintenance doses of 1 mg every 12 hours, 2 mg every 24 hours and 1 mg every 24 hours.

U.S. Pat. No. 5,663,145 also describes corresponding pharmaceutical packs contain the active substance in an initial dose in the amount from 1-60 mg in a lyophilisate ampoule, and in a maintenance dose either in one or more lyophilisate ampoules containing a sustained-release form having a delivery rate of 0.1-10 mg/day for the entire therapy period or in lyophilisate ampoules with the amount of active substance which is not present in sustained-release form in an amount from 0.1-10 mg.

However, treatment according to U.S. Pat. No. 5,663,145 fails to prevent undesired hormone withdrawal symptoms, such as flare-ups, since complete hormone suppression (chemical castration) is effected and maintained for extended time over both periods of initial dose and maintenance dose treatment. Furthermore, insufficient initial dose are applied (1 to 60 mg, 10 mg as exemplified) whereby daily application of maintenance doses are necessitated. Such daily administration of maintenance doses of LHRH antagonist needed results in 30 injections per months, which is very inconvenient for the patients treated (patient compliance) and disadvantageous from an economical point of view (associated treatment costs).

U.S. Pat. No. 6,455,499 is directed to methods of treating disorders associated with LHRH activity. The treatment of prostate cancer, breast cancer and ovarian cancer is mentioned.

Example 6 describes a treatment regimen using compound #3827, where male rats are treated with among others initial doses of 300 µg/kg/day or 1000 µg/kg/day, which effect complete castration of the rats. Subsequently the animals were further treated with "low doses" of 5 µg/kg/day, 15 µg/kg/day or 50 µg/kg/day over 21 days. However, it is explicitly stated that all treated animals remained fully castrated over the entire treatment period.

Behre H M et al. describe high loading and low maintenance doses of GnRH antagonists whereby a suppression of initial high doses can be maintained by low dose injections (Behre H M et al., J. Clin. Endocrin. Metabol. 1997, 82(5): 1403-1408). The authors show that during the low maintenance dose period LH levels, FSH levels and testosterone levels were near the assay detection limit. Testosterone levels did at no time point exceed 2 nmol/L (page 1406, left column), which equals to 0.58 ng/mL testosterone ($MW_{testosterone}$=288.43 g/mol). Therefore, it is clear from the disclosure of Behre et al. that complete castration was achieved and maintained over both periods of initial dose and maintenance dose treatment.

OBJECTS OF THE INVENTION

Objects of the present invention include the provision of novel treatments for hormone-dependent cancers, in particular prostate cancer, prostate carcinoma and/or advanced prostate carcinoma, by which negative hormone withdrawal symptoms are either prevented or at least reduced to an absolute necessary minimum. It is another object of the present invention to provide novel treatments for hormone-dependent cancers which render the daily drug administration dispensable.

SUMMARY OF THE INVENTION

The above objects of the invention have been surprisingly provided in one aspect by providing an LHRH analogue and an LHRH antagonist that can be used for the treatment or prophylaxis of hormone-dependent cancers.

DETAILED DESCRIPTION OF THE PREFERRED EMBODIMENTS

In a preferred embodiment the treatment or prophylaxis comprises:
  a) administering an initial dose of an LHRH analogue over a first period, the dose being sufficient to effect hormonal castration,
  b) then, administering a maintenance dose of an LHRH antagonist over a second period, the dose being insufficient to achieve and/or maintain hormonal castration,
  c) optionally, repeating steps a) and b).

In a preferred embodiment, during step a) hormonal castration is effected and during step b) hormonal castration is not maintained. That is hormone blood levels, in particular of LH, FSH and/or testosterone, preferably testosterone blood levels, do not remain in the castration range but recover to values above the castration range during the period of step b). With regard to testosterone blood levels, this means that during the period of step b) testosterone blood levels preferably recover to values above 1.2 ng/mL, preferably 0.58 ng/mL, most preferably 0.5 ng/mL.

In another preferred embodiment, during step a) individual blood levels of Prostate Specific Antigen (PSA) of each person are equal or below 20 ng/mL, preferably equal or below 10 ng/mL, more preferably equal or below 4 ng/mL and most preferably equal or below 3 ng/mL. Optionally, in addition during step b) hormonal castration is not maintained, i.e. hormone blood levels recover to values above the castration range as defined supra.

In yet another preferred embodiment, in addition during step b) at least temporarily individual blood levels of Prostate Specific Antigen (PSA) of each person are equal or below 20 ng/mL, preferably equal or below 10 ng/mL, more preferably equal or below 4 ng/mL and most preferably equal or below 3 ng/mL. Optionally, in addition during step b) hormonal castration is not maintained, i.e. hormone blood levels recover to values above the castration range as defined supra.

In this connection, the term "at least temporarily" refers to the fact, that individual blood levels of Prostate Specific Antigen (PSA) can be, but do not necessarily have to be equal or below the herein disclosed values over the entire period of step b). For instance, at the beginning of step b) individual blood levels of Prostate Specific Antigen (PSA) can be equal or below the herein disclosed values, then raise and at the end of period b) can be above the herein disclosed values. Such a raise above the herein disclosed values can, for instance, indicate the end of period b).

In a further preferred embodiment, the LHRH antagonist of step b) is selected from the group consisting of: "abarelix, antide, azaline B, A-75998, cetrorelix, degarelix, detirelix, ozarelix (D-63153), ganirelix, Nal-Glu-Antagonist, ramorelix, RS-68439, teverelix" and preferably is ozarelix (D-63153). In all cases, more than one LHRH antagonist can be used.

In another preferred embodiment, the LHRH analogue of step a) is an LHRH antagonist, preferably selected from the group consisting of: "abarelix, antide, azaline B, A-75998, cetrorelix, degarelix, detirelix, ozarelix (D-63153), ganirelix, Nal-Glu-Antagonist, ramorelix, RS-68439, teverelix" and most preferably is ozarelix (D-63153).

In yet another preferred embodiment, the LHRH analogue of step a) is an LHRH agonist and preferably selected from the group consisting of: "goserelin, leuprorelin (leuprolide), triptorelin, buserelin, nafarelin, historelin, deslorelin". In all cases, more than one LHRH analogue can be used.

The first period of step a) can comprise any length in days, weeks, months or years, for example 14 days, 2 weeks, 1 month, 2 years, 3 years, 4 years. In a preferred embodiment the first period in step a) comprises 1, 2, 3, 4, 5, 6, 7, 8, 9, 10, 11 or 12 months and preferably comprises 3, 4, 5, 6, 7, 8 or 9 months.

The second period of step b) can comprise any length in days, weeks, months or years for example 14 days, 2 weeks, 1 month, 2 years, 3 years, 4 years. In a preferred embodiment the second period in step b) comprises 1, 2, 3, 4, 5, 6, 7, 8, 9, 10, 11 or 12 months and preferably comprises 3, 4, 5, 6, 7, 8 or 9 months.

Steps a) and b) can optionally be repeated as often as necessary for achieving therapeutic benefits, for instance once, twice, three-times, four-times, or continuously (chronic treatment). A person skilled in the art is able due to his expert knowledge and in view of this disclosure to assess if and for how long repetition of steps a) and b) is required. Preferred is continuous repetition in the course of a chronic treatment, in particular for the treatment of prostate cancer, prostate carcinoma and/or advanced prostate carcinoma.

In yet another preferred embodiment, the second period of step b) lasts from the end of the first period in step a) until individual blood levels of Prostate Specific Antigen (PSA) of each person treated raise to equal or above 20 ng/mL, preferably equal or above 10 ng/mL, more preferably equal or above 4 ng/mL and most preferably equal or above 3 ng/mL.

Determination of individual blood levels of PSA before, during and/or after the courses of treatment can be performed by standard molecular-diagnostic procedures that are well known to the person skilled in the art.

The treatments of the present invention are surprisingly characterized in that the people treated do not show hormone withdrawal symptoms—at least during the second period of treatment [step b)].

What is more, it was found that during the second period of step b) the applied maintenance doses of LHRH antagonists are sufficiently low to prevent hormonal castration, in particular testosterone castration, i.e. without effecting the undesired castration side effects (hormone withdrawal symptoms), while still achieving the desired therapeutic effects, such as maintained low individual PSA levels, inhibition of tumor progression and/or tumor regression.

Even more surprisingly, it could be observed that such therapeutic benefits are still achievable when hormone levels, in particular testosterone levels, raise or even reach initial values (before start of treatment) as long as low PSA blood levels are maintained. With "low PSA blood levels" it is meant that individual PSA blood levels of each person treated are significantly reduced, for instance below 20 ng/mL, preferably below 10 ng/mL, more preferably below 4 ng/mL and most preferably below 3 ng/mL.

The advantageous treatment regimen of the present invention allows for a monthly or even as little as two-/three-/four-/five or six-monthly application of initial and/or maintenance doses which is likely to be due to the optimized dose schedule: high and/or effective initial dose followed by a low, but therapeutic-effect-maintaining maintenance dose. Thereby, a significantly improved patient compliance can be achieved (no castration side effects, reduced drug administration).

If an LHRH agonist is applied as initial dose in step a), an additional advantageous dose reduction can be achieved resulting in an even further improved patient compliance and reduced costs of goods.

In a preferred embodiment, the maintenance dose of the LHRH antagonist administered in step b) is 1 mg to 65 mg, preferably is 5 mg to 50 mg, more preferably is 5 mg to 40 mg, more preferably is 20 mg to 50 mg, more preferably is 20 mg to 40 mg and most preferably is selected from the following values: "5 mg, 10 mg, 15 mg, 20 mg, 25 mg, 30 mg, 35 mg, 40 mg, 45 mg, 50 mg, 55 mg, 60 mg, 65 mg".

Further it is preferred that the maintenance dose is administered as a monthly single dose every 4 weeks, as a single dose every two months, as a single dose every three months, as a single dose every four months, as a single dose every five months and/or as a single dose every six months and preferably is administered as a monthly single dose every 4 weeks or as a single dose every three months.

In another preferred embodiment, the initial dose is administered as a monthly single dose every 4 weeks, as a single dose every two months, as a single dose every three months, as a single dose every four months, as a single dose every five months and/or as a single dose every six months and preferably is administered as a monthly single dose every 4 weeks, as a single dose every three months and/or as a single dose every six months.

In yet another preferred embodiment, the initial dose of the LHRH antagonist administered in step a) is 65 mg to 300 mg, preferably is 100 mg to 250 mg and most preferably is selected from the following values: "100 mg, 130 mg, 150 mg 165 mg, 180 mg, 200 mg, 250 mg".

In a further embodiment, the initial dose of the LHRH agonist administered in step a) is 1 mg to 30 mg and preferably is 3 mg to 25 mg, for instance 3.75 mg or 11.25 mg.

In the course of the present invention, the terms "hormone" and "hormonal" within for instance "hormone castration", "hormonal castration" or "hormone withdrawal symptoms" refer to follicle stimulating hormone (FSH), luteinizing hormone (LH) and/or testosterone. Preferably, the hormonal castration is a testosterone castration and refers to a testosterone blood level of equal or below 1.2 ng/mL, preferably 0.58 ng/mL, most preferably 0.5 ng/mL.

As described earlier, the LHRH analogue and LHRH antagonist can be used for the manufacturing of a medicament for the treatment or prophylaxis of hormone-dependent cancers. Such hormone-dependent cancers can comprise any cancer which can be treated by modulation of individual FSH, LH and/or testosterone levels. In a preferred embodiment these hormone-dependent cancers are selected from the group consisting of: "prostate cancer, prostate carcinoma and/or advanced prostate carcinoma".

Corresponding medicaments containing or consisting of the LHRH analogue and LHRH antagonist as defined herein according to all herein described embodiments for use in the treatment or prophylaxis of hormone-dependent cancers, in particular prostate cancer, prostate carcinoma and/or advanced prostate carcinoma are also comprised by the present invention.

In another aspect, the object of the invention has been surprisingly solved by providing a pharmaceutical kit comprising one or more initial doses of an LHRH analogue in one or more containers, each in an amount sufficient to effect hormonal castration, and one or more maintenance doses of an LHRH antagonist in one or more containers, each in an amount insufficient to achieve and/or maintain hormonal castration.

In a preferred embodiment, the LHRH antagonist is selected from the group consisting of: "abarelix, antide, azaline B, A-75998, cetrorelix, degarelix, detirelix, ozarelix (D-63153), ganirelix, Nal-Glu-Antagonist, ramorelix, RS-68439, teverelix" and preferably is ozarelix (D-63153).

In another preferred embodiment, the LHRH analogue is an LHRH antagonist, preferably selected from the group consisting of: "abarelix, antide, azaline B, A-75998, cetrorelix, degarelix, detirelix, ozarelix (D-63153), ganirelix, Nal-Glu-Antagonist, ramorelix, RS-68439, teverelix" and most preferably is ozarelix (D-63153).

In yet another preferred embodiment, the LHRH analogue is an LHRH agonist and preferably selected from the group consisting of: "goserelin, leuprorelin (leuprolide), triptorelin, buserelin, nafarelin, historelin, deslorelin".

In a further embodiment, the pharmaceutical kit comprises one or more initial doses of an LHRH analogue in one or more containers, each in an amount sufficient to effect hormonal castration, and one or more maintenance doses of an LHRH antagonist in one or more containers, each in an amount insufficient to achieve and/or maintain hormonal castration, wherein each maintenance dose of the LHRH antagonist independently is 1 mg to 65 mg, preferably is 5 mg to 50 mg, more preferably is 5 mg to 40 mg, more preferably is 20 mg to 50 mg, more preferably is 20 mg to 40 mg and most preferably is selected from the following values: "5 mg, 10 mg, 15 mg, 20 mg, 25 mg, 30 mg, 35 mg, 40 mg, 45 mg, 50 mg, 55 mg, 60 mg, 65 mg".

In yet a further embodiment, the pharmaceutical kit comprises one or more initial doses of an LHRH analogue in one or more containers, each in an amount sufficient to effect hormonal castration, and one or more maintenance doses of an LHRH antagonist in one or more containers, each in an amount insufficient to achieve and/or maintain hormonal castration, wherein each initial dose of the LHRH antagonist independently is 65 mg to 300 mg, preferably independently is 100 mg to 250 mg and most preferably independently is selected from the following values: "100 mg, 130 mg, 150 mg 165 mg, 180 mg, 200 mg, 250 mg".

In yet another embodiment, the pharmaceutical kit comprises one or more initial doses of an LHRH analogue in one or more containers, each in an amount sufficient to effect hormonal castration, and one or more maintenance doses of an LHRH antagonist in one or more containers, each in an amount insufficient to achieve and/or maintain hormonal castration, wherein each initial dose of the LHRH agonist independently is 1 mg to 30 mg an preferably is 3 mg to 25 mg.

Preferably, such pharmaceutical kits are for use in the treatment or prophylaxis of hormone-dependent cancers selected from the group consisting of: "prostate cancer, prostate carcinoma and/or advanced prostate carcinoma".

For the purpose of the present invention, regarding the herein disclosed uses, methods of treatment, medicaments and/or pharmaceutical kits, all mammalian species are included, and referred to in the alternative herein as mammals and patients. Preferably, such mammals are selected from the group consisting of "human, domestic animals, cattle, livestock, pets, cow, sheep, pig, goat, horse, pony, donkey, hinny, mule, hare, rabbit, cat, dog, guinea pig, hamster, rat, mouse". More preferably, such mammals are human.

LHRH agonists and LHRH antagonists can be prepared for use according to the present invention as illustrated in the relevant prior art. In this connection, both LHRH agonists and LHRH antagonists can be present in fast-release or slow-release (depot) formulations. Slow-release (depot) formulations are preferred for both LHRH analogue types in order to ensure a patient-friendly treatment scheme.

Cetrorelix, for instance, can be administered in its acetate salt form, as a reconstitute of a lyophilisate (see EP 0 611 572 for preparation and process). Alternatively and preferred, it can also be applied as a slightly soluble pamoate microparticle formulation (WO 95/15767), pamoate salt (WO 02/14347) or pamoate suspension (WO 2006/069641), the latter being most preferred.

Ozarelix, for instance, can be prepared and administered as disclosed in WO 00/55190 and WO 2004/030650.

Initial dose(s) and maintenance dose(s) are packed together in an outer packaging such that an adequate amount of substance for, for example, a one-month, three-month or six-month therapy is provided.

In a preferred embodiment of the present invention:

a) first an initial dose of an LHRH analogue, i.e. an LHRH agonist or an LHRH antagonist, is administered over a first period, preferably the intervals indicated above, the dose being sufficient to effect hormonal castration. In particular it is aimed at achieving testosterone castration, i.e. reduce blood levels of testosterone to values below 1.2 ng/mL. This administration of the first initial dose provides a strong therapeutic effect at the expense of hormonal castration, b) during a second period, a maintenance dose of an LHRH antagonist is administered. By this administration the therapeutic effects induced during the first phase are maintained while the dose is insufficient to achieve or maintain hormonal castration. In a preferred situation testosterone blood levels rise to normal physiological levels again.

The active compounds in step a) and step b) above, and in fact in all embodiments of the invention, can be identical, i.e. both an LHRH antagonist, or they can be different –LHRH agonist and LHRH antagonist. In either case the dose applied is different.

As for case one, the compounds in step a) and b) are both LHRH antagonists, which can be in principle identical, i.e. cetrorelix applied in both steps or for instance cetrorelix applied in step a) and ozarelix applied in step b). If the identical compound, for instance cetrorelix, is applied in step a) and step b), only the dose of administration in both steps is different since during the first step hormonal castration is achieved whereas during the second step the dose is insufficient to effect hormonal castration.

EXAMPLES

Example 1

130 mg ozarelix is given as a single monthly initial dose per i.m. injection every 4 weeks to patients suffering from prostate cancer for a first period of 3 months. During that treatment period testosterone levels quickly reach castration level and PSA levels can be decreased by up to 95%. Subsequently, patients are treated with single monthly maintenance doses of 30 mg ozarelix given per i.m. injection over a period of 6 months. During that second period testosterone levels recover to values above 0.5 ng/mL, whereas PSA levels remain stably low until the end of the second period where they start to raise again. The treatment scheme is then repeated continuously (chronic treatment).

Example 2

200 mg ozarelix is given as a single initial dose per i.m. injection once every 3 months to patients suffering from prostate cancer for a first period of 3 to 6 months. During that treatment period testosterone levels quickly reach castration level and PSA levels can be decreased by up to 95%. Subsequently, patients are treated with single monthly maintenance doses of 40 mg ozarelix given per i.m. injection over a period of 6 months. During that second period testosterone levels recover to values above 0.5 ng/mL, whereas PSA levels remain stably low until the end of the second period where they start to raise again. The treatment scheme is then repeated continuously (chronic treatment).

Example 3

3.75 mg leuprorelin (leuprolide) are given as a single monthly initial dose per i.m. injection every 4 weeks to patients suffering from prostate cancer for a first period of 6 months. During that treatment period testosterone levels quickly reach castration level and PSA levels can be decreased by up to 95%. Subsequently, patients are treated with single monthly maintenance doses of 20 mg ozarelix given per i.m. injection over a period of 9 months. During that second period testosterone levels recover to values above 0.5 ng/mL, whereas PSA levels remain stably low until the end of the second period where they start to raise again. The treatment scheme is then repeated continuously (chronic treatment).

Example 4

11.25 mg leuprorelin (leuprolide) are given as a single initial dose per i.m. injection once every three months to patients suffering from prostate cancer for a first period of 3 months. During that treatment period testosterone levels quickly reach castration level and PSA levels can be decreased by up to 95%. Subsequently, patients are treated with single monthly maintenance doses of 50 mg ozarelix given per i.m. injection over a period of 3 months. During that second period testosterone levels recover to values above 0.5 ng/mL, whereas PSA levels remain stably low until the end of the second period where they start to raise again. The treatment scheme is then repeated continuously (chronic treatment).

The above written description of the invention provides a manner and process of making and using it such that any person skilled in this art is enabled to make and use the same, this enablement being provided in particular for the subject matter of the appended claims, which make up a part of the original description and including a method for the treatment or prophylaxis of hormone-dependent cancers, comprising:

a) administering to a patient in need thereof an initial dose of at least one LHRH analogue over a first period, the total amount of LHRH analogue in the dose being sufficient to effect hormonal castration, b) then, after administering an initial dose of said at least one LHRH analogue over a first period, administering a maintenance dose of at least one LHRH antagonist over a second period, the total amount of LHRH antagonist in the dose being insufficient to achieve and/or maintain hormonal castration.

As used herein, the phrases "selected from the group consisting of," "chosen from," and the like include mixtures of the specified materials. Terms such as "contain(s)" and the like as used herein are open terms meaning 'including at least' unless otherwise specifically noted. Phrases such as "mention may be made," etc. preface examples of materials that can be used and do not limit the invention to the specific materials, etc., listed.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A method for the treatment of hormone-dependent cancers comprising a first period and a second period; wherein hormonal castration as indicated by a testosterone blood level of 1.2 ng/mL or lower is not maintained during the second period, comprising:
   a) administering to a patient in need thereof an initial dose of at least one LHRH analogue over the first period, the total amount of LHRH analogue in the dose being sufficient to effect hormonal castration such that a testosterone blood level is less than 1.2 ng/ml, wherein the initial dose is 65 mg to 300 mg, followed by
   b) administration of a maintenance dose of at least one LHRH antagonist in an amount of from 1 to 65 mg over the second period which comprises at least 30 days, the total amount of LHRH antagonist in the maintenance dose being insufficient to achieve or maintain a testosterone blood level of 1.2 ng/mL or lower, and wherein at least temporarily the patient's individual blood level of Prostate Specific Antigen (PSA) is equal to or below 20 ng/ml.

2. The method according to claim 1, wherein the patient is a human.

3. The method according to claim 1, wherein dose of the at least one LHRH antagonist comprises at least one compound selected from the group consisting of abarelix, antide, azaline B, A-75998, cetrorelix, degarelix, detirelix, ozarelix (D-63153), ganirelix, Nal-Glu-Antagonist, ramorelix, RS-68439, teverelix.

4. The method according to claim 1, wherein the dose of the at least one LHRH analogue comprises at least one LHRH antagonist selected from the group consisting of abarelix, antide, azaline B, A-75998, cetrorelix, degarelix, detirelix, ozarelix (D-63153), ganirelix, Nal-Glu-Antagonist, ramorelix, RS-68439, teverelix.

5. The method according to claim 1, wherein the dose comprising at least one LHRH analogue of a) comprises at least one LHRH agonist selected from the group consisting of goserelin, leuprorelin (leuprolide), triptorelin, buserelin, nafarelin, historelin, and deslorelin.

6. The method according to claim 1, wherein in a) the first period comprises 1, 2, 3, 4, 5, 6, 7, 8, 9, 10, 11 or 12 months.

7. The method according to claim 1, wherein in b) the second period comprises 1, 2, 3, 4, 5, 6, 7, 8, 9, 10, 11 or 12 months.

8. The method according to claim 1, wherein the patient is a human and wherein in b) the second period lasts from the end of the first period in a) until the patient's individual blood level of Prostate Specific Antigen (PSA) rise to equal or above 20 ng/mL.

9. The method according to claim 1, wherein the maintenance dose is administered as a monthly single dose every 4 weeks, as a single dose every two months, as a single dose every three months, as a single dose every four months, as a single dose every five months and/or as a single dose every six months.

10. The method according to claim 1, wherein the initial dose is administered as a monthly single dose every 4 weeks, as a single dose every two months, as a single dose every three months, as a single dose every four months, as a single dose every five months and/or as a single dose every six months.

11. The method according to claim 1, further comprising repeating a) and b) continuously.

12. The method according to claim 1, wherein the hormone-dependent cancer is selected from the group consisting of prostate cancer, prostate carcinoma and advanced prostate carcinoma.

* * * * *